United States Patent [19]

Mizukami et al.

[11] Patent Number: 5,972,997
[45] Date of Patent: Oct. 26, 1999

[54] UCT1072 COMPOUNDS

[75] Inventors: Tamio Mizukami, Tokyo; Akira Asai, Kanagawa; Katsuhiko Ando, Tokyo; Shingo Kakita, Tokyo; Akira Mihara, Tokyo; Katsunori Kita, Shizuoka; Yasuhiro Suzuki, Shizuoka; Tadashi Ashizawa, Shizuoka, all of Japan

[73] Assignee: Kyowa Hakko Kogyo Co., Ltd., Tokyo, Japan

[21] Appl. No.: 08/930,852

[22] PCT Filed: Feb. 6, 1997

[86] PCT No.: PCT/JP97/00282

§ 371 Date: Oct. 3, 1997

§ 102(e) Date: Oct. 3, 1997

[87] PCT Pub. No.: WO97/29099

PCT Pub. Date: Aug. 14, 1997

[30] Foreign Application Priority Data

Feb. 6, 1996 [JP] Japan .................................. 8-019675

[51] Int. Cl.$^6$ .................................................. A01N 43/08
[52] U.S. Cl. ............................................ 514/468; 549/456
[58] Field of Search ............................. 549/456; 514/468

[56] References Cited

FOREIGN PATENT DOCUMENTS

| 0 664 295 | 7/1995 | Germany . |
| 0 380 373 | 8/1990 | Japan . |
| 0 657 412 | 6/1995 | Japan . |

OTHER PUBLICATIONS

Anderson et al., ""Versicolorin A hemiacetal, hydroxydihydrosterigmatocystin, and aflatoxin G2a reductase activity in extracts from Aspergillus parasiticus"", Mycopathologia 111:39–45, 1990.

Sean M. McGuire et al. (J. Am. Chem. Soc.), vol. 111, No. 21, (1989), pp. 8308–8309.

John A. Anderson et al. (Mycopathologia), vol. 111, No. 1, (1990), p. 39–45.

CRC Handbook Of Antibiotic Compounds, Vol. III, Janos Berdy, et al.

*Primary Examiner*—Dwayne C. Jones
*Attorney, Agent, or Firm*—Fitzpatrick, Cella, Harper & Scinto

[57] ABSTRACT

The present invention relates to UCT1072 compounds represented by formula (I):

wherein $R^1$ and $R^2$ together represent —CH(OH)CH$_2$O— or —CH$_2$CH$_2$CH(OH)CH$_2$—.

12 Claims, No Drawings

UCT1072 COMPOUNDS

CROSS-REFERENCES TO RELATED APPLICATIONS

This application is a 371 of PCT/JP 97/00282, filed Feb. 6, 1997, which claims priority benefit of JP 8-19675, filed Feb. 6, 1996.

STATEMENT REGARDING FEDERALLY SPONSORED RESEARCH DEVELOPMENT

Not Applicable

MICROFICHE APPENDIX

Not Applicable

BACKGROUND OF THE INVENTION

1. Field of the Invention

The present invention relates to compounds which have antitumor activity and are useful as antitumor agents.

2. Description of the Related Art

Several compounds such as anthracycline and the like have been reported as antibiotics which have the anthraquinone nucleus (CRC Handbook of Antibiotic Compounds, CRC Press, U.S.A., 1981).

BRIEF SUMMARY OF THE INVENTION

The present invention relates to UCT1072 compounds.

BRIEF DESCRIPTION OF THE DRAWINGS

Not Applicable

DETAILED DESCRIPTION OF THE INVENTION

The present invention provides UCT1072 compounds represented by formula (I):

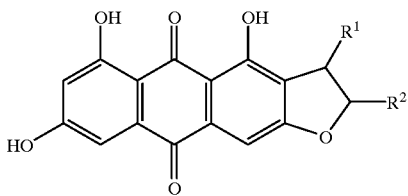

wherein $R^1$ and $R^2$ together represent —CH(OH)CH$_2$O— or —CH$_2$CH$_2$CH(OH)CH$_2$—, which has antitumor activity. The compounds can be obtained by culturing a microorganism belonging to the genus Aspergillus.

Among the UCT1072 compounds represented by formula (I), the compound in which $R^1$ and $R^2$ together represent —CH(OH)CH$_2$— is called UCT1072M1, and the compounds in which $R^1$ and $R^2$ together represent —CH$_2$CH$_2$CH(OH)CH$_2$— are called UCT1072M2 and UCT1072M3. UCT1072M2 and UCT1072M3 are respective stereoisomers.

The physicochemical properties of UCT1072 compounds are shown below. The physicochemical properties were measured by the following apparatus:

Mass spectrum:
  JEOL: JMS-HX/HX110A mass spectrometer
Ultraviolet absorption spectrum:
  Shimadzu Corporation: UV-2200 spectrophotometer
Infrared absorption spectrum:
  JEOL: JIR-RFX3001 infrared spectrophotometer
Nuclear magnetic resonance spectrum:
  JEOL: JNM-A400 nuclear magnetic resonance apparatus
  Bruker: AM500 nuclear magnetic resonance apparatus
Optical rotation:
  Nippon Bunko Kogyo: DIP-370 type digital polarimeter
Melting point:
  Yanagimoto Seisakusyo: Micro measuring apparatus of melting point Physicochemical data of UCT1072M1:
  Color and form of the substance:
    Yellow solid
  Melting point:
    No change up to 300° C.
  Optical rotation:
    $[\alpha]^{26}_{577}=-356°$ [c=0.274, dimethylsulfoxide (DMSO)]
  Ultraviolet absorption spectrum:
    $\lambda_{max}$ (DMSO) nm ($\epsilon$) 292 (22000), 330 (11000), 456 (5600)
  Infrared absorption spectrum:
    $\upsilon_{max}$ (KBr) cm$^{-1}$ 3410, 1628, 1308, 1296, 1190, 1024
  Molecular formula:
    $C_{18}H_{12}O_8$
  Molecular weight:
    356
  FAB mass spectrum (positive mode):
    m/z 357 (M+H)$^+$
  High resolution FAB mass spectrum (positive mode):
    m/z 357.0601 (M+H)$^+$(calculated for $C_{18}H_{13}O_8$:357.0610)
  $^1$H NMR spectrum (500 MHz, DMSO-d$_6$): δ ppm
    3.59, 3.90, 3.95, 4.45, 5.62, 6.58, 6.63, 7.06, 7.10, 12.06, 12.45
  $^{13}$C NMR (125 MHz, DMSO-d$_6$): δ ppm 53.3(d), 72.8(d), 74.9(t), 101.5(d), 108.1(d), 108.5(s), 109.0(d), 110.8(s), 113.0(d), 117.4(s), 134.8(s), 135.6(s), 159.4(s), 164.3(s), 165.28 (s), 165.33(s), 180.9(s), 189.1(s)
  Color reagent:
    Iodine reagent
  Thin-layer chromatography:
    Rf value:
      0.5
    Thin-layer:
      silicagel TLC (produced by Merck Co.)
    Developing solvent:
      chloroform:methanol=10:1

Physicochemical data of UCT1072M2:
  Color and form of the substance:
    Yellow solid
  Melting point:
    241–242° C.
  Optical rotation:
    $[\alpha]^{26}_{577}=-720°$ (c=0.174, DMSO)
  Ultraviolet absorption spectrum:
    $\lambda_{max}$ (DMSO) nm ($\epsilon$) 294 (36000), 333 (14000), 459 (8400)
  Infrared absorption spectrum:
    $\upsilon_{max}$ (KBr) cm$^{-1}$ 3420, 1628, 1608, 1394, 1385, 1309, 1288
  Molecular formula:
    $C_{20}H_{16}O_7$ Molecular weight:
  368
FAB mass spectrum (positive mode):
  m/z 369 (M+H)$^+$
High resolution FAB mass spectrum (positive mode):
  m/z 369.0993 (M+H)+(calculated for $C_{20}H_{17}O_7$:369.0975)
$^1$H NMR (400 MHz, DMSO-d$_6$): δ ppm
  1.30, 1.63, 1.70, 1.77, 2.12, 2.16, 3.56, 3.67, 4.60, 5.02, 6.58, 7.08, 7.12, 12.12, 12.40
$^{13}$C NMR (100 MHz, DMSO-d$_6$): δ ppm
  20.7(t), 30.0(t), 35.6(t), 38.1(d), 63.2(d), 83.8(d), 102.8 (d), 108.0(d), 108.6(s), 108.8(d), 110.8(s), 123.1(s), 134.9(s), 135.2(s), 159.8(s), 164.2(s), 165.2(s), 166.0(s), 181.0(s), 189.3(s)
Color reagent:
  Iodine reagent
Thin-layer chromatography:
Rf value:
  0.7
Thin-layer:
  silicagel TLC (produced by Merck Co.)
Developing solvent:
  chloroform:methanol=10:1

Physicochemical data of UCT1072M3:
Color and form of the substance:
  Yellow solid
Melting point:
  160–163° C.
Optical rotation:
  [α]$^{26}_{577}$=+64.8° (c=0.174, DMSO)
Ultraviolet absorption spectrum:
  λ$_{max}$ (DMSO) nm 293 (20000), 332 (9300), 459 (4700)
Infrared absorption spectrum:
  ν$_{max}$ (KBr) cm$^{-1}$ 3344, 1624, 1311, 1294
Molecular formula:
  $C_{20}H_{16}O_7$
Molecular weight:
  368
FAB mass spectrum (positive mode):
  m/z 369 (M+H)$^+$
High resolution FAB mass spectrum:
  m/z 369.0987 (M+H)$^+$ (calculated for $C_{20}H_{17}O_7$:369.0975)
$^1$H NMR (400 MHz, DMSO-d$_6$) δ ppm:
  1.26, 1.26, 1.71, 1.75, 2.11, 2.32, 3.38, 3.67, 4.79, 4.98, 6.58, 7.10, 7.11, 12.12, 12.31
$^{13}$C NMR (100 MHz, DMSO-d$_6$) δ ppm:
  25.1(t), 31.1(t), 35.5(t), 36.7(d), 63.9(d), 86.1(d), 102.7 (d), 108.0(d), 108.6(s), 108.9(d), 110.9(s), 125.9(s), 134.9(s), 135.1(s), 158.9(s), 164.3(s), 165.2(s), 165.5(s), 181.1(s), 189.3(s)
Color reagent:
  Iodine reagent
Thin-layer chromatography:
Rf value:
  0.65
Thin-layer:
  silicagel TLC (produced by Merck Co.)
Developing solvent:
  chloroform:methanol=10:1

Biological activities of the UCT1072 compounds are described by the following test examples.

TEST EXAMPLE 1
Growth Inhibition of UCT1072 on Human Uterine Cancer HeLa S3 Cells and Human Lung Cancer Lu-65 Cells Respective cells were dispensed in 3×10$^3$ cells/well portions into a 96 well microtiter plate (produced by Nunc Co., #167008) and pre-cultured at 37° C. for 24 hours in a 5% carbon dioxide incubator. Thereafter, 3 mM solution of UCT1072M1, UCT1072M2 or UCT1072M3 was serially diluted and dispensed in 50 μl portions into the wells. In this example, final concentrations of UCT1072 in each solution are at most 0.013 μM. Culturing was continued at 37° C. for 72 hours in the 5% carbon dioxide incubator. Four hours prior to the completion of the culturing, XTT [2,3-bis(2-methoxy-4-nitro-5-sulfophenyl)-5-[(phenylamino)-carbonyl]-2H-tetrazolium hydroxide, produced by Polysciences Co.] containing 0.5% 1-methoxyphenazine methosulfate (produced by Sigma Co.) was dispensed in 25 μl/well portions into the culture medium to a final concentration of 1 mg/ml. After completion of the culturing, absorbance at 492 nm was measured using Microplate Reader MTP-32 (produced by Corona Electric Co.). The cell growth inhibition activity was expressed by 50% growth inhibition concentration IC$_{50}$.

The results are shown in Table 1.

TABLE 1

| | IC$_{50}$ (μM) | |
|---|---|---|
| Compound | HeLa S3 | Lu-65 |
| UCT1072M1 | 2.1 | 2.2 |
| UCT1072M2 | 8.9 | >10 |
| UCT1072M3 | 2.7 | 3.2 |

TEST EXAMPLE 2
Antitumor Effect on Sarcoma 180 Tumor

Using 5 animals per group of ddY male mice, 5×10$^6$ of sarcoma 180 tumor cells were transplanted under the axillary subcutaneously. First, 1 mg of the compound UCT1072M1 to be used as a test compound was mixed with 10 μl of Tween 80 and suspended in 0.3% CMC (carboxymethyl cellulose), and the suspension was administered intraperitoneally for 5 days starting on the day after the tumor transplantation. After 7 days following tumor transplantation, mean tumor volume (mm$^3$) and antitumor activity (T/C) were measured. The antitumor activity was calculated by the following formula.

$$\text{Antitumor activity} = \frac{\text{mean tumor volume (mm}^3\text{) in test plot}}{\text{mean tumor volume (mm}^3\text{) in control plot}}$$
$$\text{(administration of physiological saline)}$$

The results are shown in Table 2.

TABLE 2

| Compound | Dosage (mg/kg/day) | Mean tumor volume (mm$^3$) | Antitumor activity (T/C) |
|---|---|---|---|
| UCT1072M1 | 0 | 2314 | 1 |
| | 4.7 | 1616 | 0.7 |
| | 9.4 | 1553 | 0.67 |
| | 19 | 1468 | 0.64 |
| | 38 | 1145 | 0.50 |
| | 75 | 1275 | 0.55 |

Next, the process for producing UCT1072 compounds is described below.

The UCT1072 compounds can be obtained by culturing in a medium a microorganism belonging to the genus Aspergillus and having the ability to produce UCT1072 compounds, thereby allowing UCT1072 compounds to accumulate in the culture, and recovering UCT1072M1, UCT1072M2 or UCT1072M3, from the culture mixture.

Any strain can be used as the microorganism capable of producing the UCT1072 compound, provided that the strain belongs to the genus Aspergillus and has the ability to produce the UCT1072 compound. In addition, any mutants of such strains which are obtained by various artificial mutation of methods such as ultraviolet ray irradiation, X-ray irradiation and mutagens treatment or by spontaneous mutation may also be used in the present invention, insofar as they have the ability to produce the UCT1072 compounds. A typical example of a suitable strain is Aspergillus sp. O-14-7 strain.

The inventors of the present invention have found that a fungal strain O-14-7 belonging to the genus Aspergillus, which has been newly isolated from a soil sample, was able to produce the antitumor agent UCT1072 compounds. The mycological properties of Aspergillus sp. O-14-7 strain are as follows.

1. Macroscopic Observation

When cultured at 25° C. on malt extract agar media, the diameter of a colony reaches 20 to 28 mm on the 7th day of the culturing and 35 to 42 mm on the 14th day of culturing. The colony shows a dark green color, its central part shows a deep grayish green color and its peripheral part shows a cream color. On the reverse side, the central part is light yellowish brown and the peripheral is brownish cream.

When cultured at 25° C. on potato-glucose agar media, the diameter of a colony reaches 25 to 30 mm on the 7th day of the culturing and 47 to 53 mm on the 14th day of culturing. The colony shows a deep grayish green color and its peripheral part shows a slightly blue-greenish ash white color. On the reverse side, the central part is dark brown and the peripheral is light brown.

This strain grows at 10 to 35° C. and the optimum growth temperature is at around 26° C. It can grow at a pH within the range of from 4 to 12, and its optimum growth pH is around 7.

2. Light Microscopic Observation of the Strain When Cultured on a Malt Extract Agar Medium Hyphae have septa, are smooth and branch. Conidiophores do not become synnematous but develop singly from each foot cell of hyphae, which are smooth and colorless or light brown in some cases, have no septum and reach 370 $\mu$m in length. Conidiophore are 3.5 to 6.5 $\mu$m width, and the wall has a width of 0.5 to 1.5 $\mu$m. A globular or oval vesicle of 14 to 19 $\mu$m long and 11.5 to 14 $\mu$m wide is formed on the tip of the conidiophore, a large number of sub-globular to cylindrical metulae are formed on its entire surface and 2 to 4 phialides are formed on the metulae. Each metula is colorless and smooth and has a length of 4.5 to 7.5 $\mu$m and a width of 2.5 to 5.5 $\mu$m. Phialides are bottle shape, 5 to 8 $\mu$m long and 2.5 to 4 $\mu$m wide at the broadest part. Ontogenetic pattern of conidia is an enteroblastic type. Conidia develop from the tip (0.5 to 1.5 $\mu$m in width) of each phialide in chain. The phialoconidium is a globular to sub-globular single cell, echinulate, 2.5 to 4.5 $\mu$m diam and the conidial mass shows olive green color.

Only the above-mentioned anamorph can be observed in the present strain and no teleomorph can be observed.

By the above mycological properties, it was identified that the taxonomic position of the present strain is Aspergillus sp. in conformity with "The Genera of Fungi Sporulating in Pure Culture, 2nd ed., Cramer, Vaduz, J. A. von Arx, 1974". The strain, named Aspergillus sp. O-14-7, has been deposited on Jan. 31, 1996, in National Institute of Bioscience and Human Technology, Agency of Industrial Science and Technology, the Ministry of International Trade and Industry (Higashi 1-1-3, Tsukuba-shi, Ibaraki, Japan), and has been assigned the designation as FERM BP-5378.

For the culturing of the UCT1072 compounds producing strains used in the present invention, conventional methods for culturing filamentous fungi are generally employed. With regard to the culture medium, either a synthetic medium or a natural medium can be used insofar as it properly contains carbon sources, nitrogen sources and inorganic substances which can be assimilated by the microorganism and the growth- and production-promoting substances required thereby.

As the carbon sources, glucose, starch, dextrin, mannose, fructose, sucrose, lactose, xylose, arabinose, mannitol, molasses and the like may be used alone or in combination. Depending on the assimilation capacity of the strain, hydrocarbons, alcohols, organic acids and the like may also be used.

As the nitrogen sources, ammonium chloride, ammonium nitrate, ammonium sulfate, sodium nitrate, urea, peptone, meat extract, yeast extract, dried yeast, corn steep liquor, soybean powder, casamino acid and the like can be used alone or in combination. In addition to these materials, inorganic salts, such as sodium chloride, potassium chloride, magnesium sulfate, calcium carbonate, potassium dihydrogen phosphate, ferrous sulfate, calcium chloride, manganese sulfate, zinc sulfate, copper sulfate and the like, may be used as occasion demands. Also, minor components which enhance growth of the strain or production of the UCT1072 compounds can be added appropriately.

As the culturing methods, a liquid culture method, particularly a submerged stirring culture method, may be employed desirably. The culturing is carried out at from 16 to 37° C., preferably 25 to 32° C., and at pH 4 to 10, preferably 6 to 8, and the adjustment of medium pH is effected by using liquid ammonia, ammonium carbonate aqueous solution or the like. The culturing is completed generally within 1 to 7 days and terminated when the UCT1072 compounds are formed and accumulated in the culture medium and cells and its amount produced in the culture mixture reaches the maximum.

The UCT1072 compounds thus accumulated in the culture mixture can be isolated and purified from the culture mixture by employing a method usually used for the isolation and purification of general microbial metabolic products from culture mixtures.

For example, the culture are separated into culture filtrate and cells by filtration, and the cells were treated with a solvent such as chloroform, acetone or the like to extract the cell components. The extract and the culture filtrate are combined and passed through a column packed with a polystyrene absorbent such as Diaion HP20 (produced by Mitsubishi Chemical Corporation), thereby effecting adsorption of the active component which is subsequently eluted with methanol, acetone or the like. The eluate is concentrated, and the UCT1072 compounds are obtained by ODS column chromatography, high-performance liquid chromatography, silica gel column chromatography or the like means. In this connection, detection of the UCT1072 compounds during the culturing and the isolation and purification steps can be effected by checking a sample with a thin layer chromatography and then using a iodine reagent.

Examples according to the present invention are described in the following.

EXAMPLE 1

Production of UCT1072M1

Aspergillus sp. O-14-7 strain was used as a seed strain.

As media for the first, second and third seed cultures, a medium composed of 200 g/l tomato-based juice (vegetable juice) and 30 g/l dextrin (pH 6.5) was used. One loopfull of the seed strain cells was inoculated into 30 ml of the first seed culture medium contained in a 250 ml capacity conical flask and cultured on a shaker at 25° C. for 72 hours.

A 5 ml portion of the 30 ml first seed culture broth was then inoculated into 300 ml of the second seed culture medium contained in each of 2 liter capacity conical flasks (a total of 6 flasks, 1.8 liters) and cultured on a shaker at 25° C. for 72 hours.

Thereafter, the thus obtained 1.8 liters of the second seed culture broth was inoculated into 100 liters of the third seed culture medium contained in a 200 liter capacity tank and cultured at 25° C. for 72 hours with aeration and agitation.

The thus obtained 100 liters of the third seed culture broth was inoculated into 1,000 liters of a main fermentation medium contained in a 2 kiloliter capacity tank, and the main fermentation medium was cultured at 25° C. for 91 hours with aeration and agitation. As the main fermentation medium, medium composed of 50 g/l soluble starch, 20 g/l corn steep liquor, 0.5 g/l potassium dihydrogen phosphate, 0.5 g/l magnesium sulfate·7H$_2$O and 5 g/l calcium carbonate (pH 7.0) was used.

A filter aid (Radiolite #600, produced by Showa Chemical Industry Co.) was then added in 10% portion to the thus obtained 1,000 liter fermentation broth to carry out filtration using a filter press. The culture filtrate was separated from cells, and the separated cells were mixed with 1,000 liters of methanol and thoroughly stirred to effect extraction and again filtered by the filter press. The thus obtained methanol extract and the culture filtrate were combined, applied to a column packed with 50 liters of Diaion HP20 (produced by Mitsubishi Chemical Corporation) and washed with 150 liters of 50% methanol aqueous solution and then the active components were eluted with 200 liters of methanol. Fractions containing M-1 were collected and concentrated to dryness under reduced pressure to obtain brown oily substances.

The brown oily substances were dissolved in 800 ml of methanol and purified by a fractional liquid chromatography using a reverse phase silica gel (ODS-AQ-50, produced by YMC Co.). The methanol solution was filtered through a glass filter (G3) to remove insoluble matter, and 200 ml of the filtrate was mixed with 50 g of ODS, concentrated to dryness under reduced pressure and then applied to a column (70 φ×500 mm) packed with 1.9 liters of ODS. This was firstly developed with 8 liters of acetonitrile/10 mM phosphate buffer pH 5.5 (3:7) solution to effect elution of impurities and then developed with 4 liters of acetonitrile/10 mM phosphate buffer pH 5.5 (4:6) solution to effect elution of the active components. In order to treat entire portion of the filtrate (800 ml), the just described chromatography was repeated 4 times. The fractions containing UCT1072M1 (for 4 times of repetition) thus obtained were collected, concentrated under reduced pressure to remove acetonitrile and then extracted with ethyl acetate and concentrated to dryness, thereby obtaining light brown oily substances.

The light brown oily substances were dissolved in 40 ml of acetone and purified by a fractional liquid chromatography using a normal phase silica gel column (Develosil Lop60 45S, 45 φ×490 mm, produced by Nomura Kagaku Co.). A 10 ml portion of the acetone solution was adsorbed to the column, developed with 800 ml of a hexane:acetone:acetic acid (100:10:1) mixture solvent to effect elution of impurities and then developed with 1,600 ml of a hexane:acetone:acetic acid (100:30:1) mixture solvent to effect elution of UCT1072M1. In order to treat entire portion of the acetone solution (40 ml), the just described chromatography was repeated 4 times. The thus obtained fractions containing UCT1072M1 (for 4 times of repetition) were collected, concentrated under reduced pressure and then extracted with ethyl acetate. The ethyl acetate layer was concentrated under reduced pressure and then mixed with hexane to effect precipitation of UCT1072M1. The thus precipitated UCT1072M1 was collected by filtration and dried to obtain 282 mg of yellow powder.

EXAMPLE 2

Production of UCT1072M2 and UCT1072M3

Aspergillus sp. O-14-7 strain was used as the seed strain.

As media for the first, second and third seed cultures, a medium composed of 200 g/l tomato-based juice (vegetable juice) and 30 g/l dextrin (pH 6.5) was used. One loopfull of the seed strain cells was inoculated into 30 ml of the first seed culture medium contained in a 250 ml capacity conical flask and cultured on a shaker at 25° C. for 72 hours.

A 5 ml portion of the 30 ml first seed culture broth was then inoculated into 300 ml of the second seed culture medium contained in each of 2 liter capacity conical flasks (a total of 6 flasks, 1.8 liters) and cultured on a shaker at 25° C. for 72 hours.

Thereafter, the thus obtained 1.8 liters of the second seed culture broth was inoculated into 100 liters of the third seed culture medium contained in a 200 liter capacity tank and cultured at 25° C. for 72 hours with aeration and agitation.

The thus obtained 100 liters of the third seed culture broth was inoculated into 1,000 liters of a main fermentation medium contained in a 2 kiloliter capacity tank, and the main fermentation medium was cultured at 25° C. for 139 hours with aeration and agitation. As the main fermentation medium, a medium composed of 50 g/l soluble starch, 20 g/l corn steep liquor, 0.5 g/l potassium dihydrogen phosphate, 0.5 g/l magnesium sulfate·7H$_2$O and 5 g/l calcium carbonate (pH 7.0) was used.

A filter aid (Radiolite #600, produced by Showa Chemical Industry Co.) was then added in 4% portion to the thus obtained 1,000 liter fermentation broth to carry out filtration using a filter press. The thus obtained culture filtrate was applied to a column packed with 50 liters of Diaion HP20 (produced by Mitsubishi Chemical Corporation) and washed with 200 liters of 80% methanol aqueous solution and then the active components were eluted with 200 liters of methanol. Fractions containing M-2 and M-3 were collected and concentrated to dryness under reduced pressure to obtain a brown oily substance.

The brown oily substance was dissolved in 1 liter of acetone, mixed with 250 g of silica gel (Wako Gel C-300, produced by Wako Pure Chemical Industries Co.), concentrated to dryness under reduced pressure and then applied to a column (200 φ×1,000 mm) packed with 10 liters of Wako Gel C-300. This was developed with 40 liters of a hexane:acetone:acetic acid (100:50:1) mixture solvent to effect elution of the active components, and fractions containing UCT1072M2 and UCT1072M3 were collected and concentrated to dryness under reduced pressure to obtain a light brown oily substance. The light brown oily substance was dissolved in a small amount of methanol and adsorbed to a column (40 φ×400 mm) packed with 500 ml of a reverse phase silica gel (ODS-AQ-50, produced by YMC Co.). This was firstly developed with 1,500 ml of acetonitrile/10 mM phosphate buffer pH 5.5 (4:6) solution to effect elution of impurities and then developed with 1,000 ml of acetonitrile/ 10 mM phosphate buffer (6:4) solution and 1,000 ml of acetonitrile/10 mm phosphate buffer (8:2) in that order to effect elution of the active components. The fractions containing UCT1072M2 and UCT1072M3 thus obtained were collected, concentrated under reduced pressure to remove acetonitrile and then extracted with ethyl acetate. The ethyl acetate layer was concentrated under reduced pressure and mixed with hexane to obtain yellow powder. The thus obtained powder was dissolved in a small amount of acetone and purified by a fractional liquid chromatography using a normal phase silica gel column (Develosil Lop6O 24S, 24 φ×360 mm, produced by Nomura Kagaku Co.). The acetone solution was adsorbed to the column and washed with 90 ml of hexane. This was developed with 500 ml of a hexane:acetone:acetic acid (100:10:1) mixture solvent to effect elution of impurities and then developed with 500 ml of a hexane:acetone:acetic acid (100:30:1) mixture solvent and 500 ml of a hexane:acetone:acetic acid (100:50:1) mixture solvent in that order to effect elution of the active components. Fractions containing UCT1072M2 and UCT1072M3 were collected, concentrated under reduced pressure and then extracted with ethyl acetate. The ethyl acetate layer was concentrated under reduced pressure and then mixed with hexane to obtain 12 mg of yellow powder.

Separation of UCT1072M2 and UCT1072M3 was carried out by a gel filtration using Sephadex LH-20 (produced by Pharmacia Biotech Co.). The powder was dissolved in a small amount of 70% methanol aqueous solution, applied to the column and then developed with the same solution. Since UCT1072M2 was eluted firstly and then UCT1072M3 a little later, fractions of UCT1072M2 and UCT1072M3 were separately collected, concentrated under reduced pressure and extracted with ethyl acetate. The acetate layers were respectively concentrated under reduced pressure and mixed with hexane to effect precipitation of UCT1072M2 and UCT1072M3. The thus precipitated UCT1072M2 and UCT1072M3 were respectively collected by filtration and dried, thereby obtaining 2 mg of yellow powder of each of UCT1072M2 and UCT1072M3.

SEQUENCE LISTING

Not Applicable.

What is claimed is:

1. An isolated and purified compound represented by formula (I):

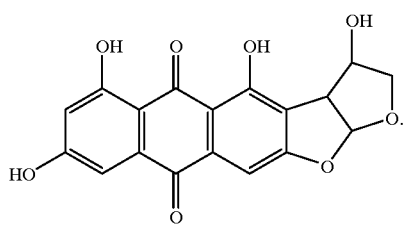

2. An isolated and purified compound represented by formula (II):

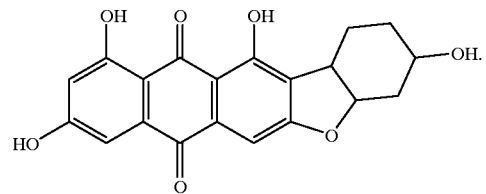

3. A pharmaceutical composition, comprising a compound according to formula (I):

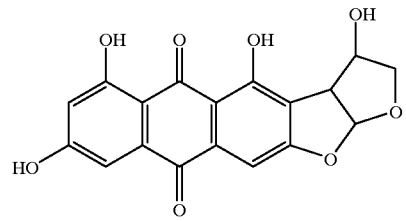

together with a pharmaceutically acceptable carrier.

4. A pharmaceutical composition, comprising a compound according to formula (II):

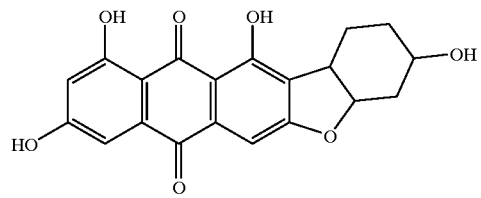

together with a pharmaceutically acceptable carrier.

5. A method of treating tumors in-humans, comprising administering to a human in need thereof a compound according to claim 1.

6. A method of treating tumors in humans, comprising administering to a human in need thereof a compound according to claim 2.

7. A method of treating tumors in humans, comprising administering to a human in need thereof a pharmaceutical composition according to claim 3.

8. A method of treating tumors in humans, comprising administering to a human in need thereof a pharmaceutical composition according to claim 4.

9. The method according to claim 5, wherein said tumor is a sarcoma, or a uterine or lung cancer.

10. The method according to claim 6, wherein said tumor is a sarcoma, or a uterine or lung cancer.

11. The method according to claim 7, wherein said tumor is a sarcoma, or a uterine or lung cancer.

12. The method according to claim 8, wherein said tumor is a sarcoma, or a uterine or lung cancer.

* * * * *

UNITED STATES PATENT AND TRADEMARK OFFICE
CERTIFICATE OF CORRECTION

PATENT NO. : 5,972,997
DATED : October 26, 1999
INVENTOR(S) : TAMIO MIZUKAMI ET AL.

It is certified that error appears in the above-identified patent and that said Letters Patent is hereby corrected as shown below:

COLUMN 1

Line 56, "—CH(OH)CH$_2$—" should read ---CH(OH)CH$_2$O---.

COLUMN 3

Line 6, "(M+H) + (calculated" should read --(M+H)$^+$ (calculated--.

COLUMN 5

Line 46, "width," should read --in width,--;
Line 58, "diam" should read --in diameter--.

COLUMN 6

Line 49, "are" should read --is--.

COLUMN 7

Line 55, "entire" should read --the entire--.

COLUMN 8

Line 4, "entire" should read --the entire--.

UNITED STATES PATENT AND TRADEMARK OFFICE
CERTIFICATE OF CORRECTION

PATENT NO. : 5,972,997
DATED : October 26, 1999
INVENTOR(S) : TAMIO MIZUKAMI ET AL.

It is certified that error appears in the above-identified patent and that said Letters Patent is hereby corrected as shown below:

COLUMN 10

Line 41, "in-humans," should read --in humans,--.

Signed and Sealed this

Twenty-first Day of November, 2000

Attest:

Attesting Officer

Q. TODD DICKINSON

Director of Patents and Trademarks